United States Patent [19]
Goldman

[11] Patent Number: 5,446,534
[45] Date of Patent: Aug. 29, 1995

[54] BROAD BAND WAVEGUIDE SPECTROMETER

[75] Inventor: Don S. Goldman, Folsom, Calif.

[73] Assignee: Optical Solutions, Inc., Folsom, Calif.

[21] Appl. No.: 27,026

[22] Filed: Mar. 5, 1993

[51] Int. Cl.⁶ .......................................... G01N 21/41
[52] U.S. Cl. ................................. 356/128; 356/326; 356/328; 385/37; 385/43; 385/130
[58] Field of Search ............... 356/128, 300, 326, 328; 385/43, 37, 36, 129, 130

[56] References Cited

U.S. PATENT DOCUMENTS

| | | | |
|---|---|---|---|
| 4,664,522 | 5/1987 | Lebebre | 355/328 |
| 4,711,514 | 12/1987 | Tangonan et al. | 350/96.12 |
| 4,815,843 | 3/1989 | Tiefenthaler et al. | 356/128 |
| 4,877,747 | 10/1989 | Stewart | 350/96.15 |
| 5,082,629 | 1/1992 | Burgess, Jr. et al. | 355/128 |
| 5,208,882 | 5/1993 | Strasser et al. | 385/43 |

FOREIGN PATENT DOCUMENTS

| | | | |
|---|---|---|---|
| 60-78406 | 5/1985 | Japan | 385/43 |
| 60-177306 | 9/1985 | Japan | 385/43 |
| 1-252907 | 10/1989 | Japan | 385/130 |

OTHER PUBLICATIONS

Radiation Fields of a Tapered Film and a Novel Film-To-Fiber Coupler-P. K. Tien; IEEE Transactions on Microwave Theory & Tech., vol. MTT-23, No. 1, Jan. 1975.

Integrated Optics-T. Tamir; Second Corrected & Updated Edition, 1979.

*Primary Examiner*—William Mintel
*Assistant Examiner*—Minhloan Tran
*Attorney, Agent, or Firm*—Bielen, Peterson & Lampe

[57] ABSTRACT

A spectrometer for analyzing a sample of material utilizing a broad band source of electromagnetic radiation and a detector. The spectrometer employs a waveguide possessing an entry and an exit for the electromagnetic radiation emanating from the source. The waveguide further includes a surface between the entry and exit portions which permits interaction between the electromagnetic radiation passing through the wave guide and a sample material. A tapered portion forms a part of the entry of the wave guide and couples the electromagnetic radiation emanating from the source to the waveguide. The electromagnetic radiation passing from the exit of the waveguide is captured and directed to a detector for analysis.

22 Claims, 5 Drawing Sheets

BROAD BAND WAVEGUIDE SPECTROMETER

The United States Government has rights to this invention pursuant to contract No. DE-FC07-911D13083 awarded by the U.S. Department of Energy.

BACKGROUND OF THE INVENTION

The present invention relates to a novel broad band spectrometer.

Thin-film optical waveguides have been successfully integrated with optical fiber technology in the telecommunication industry. U.S. Pat. Nos. 4,664,522 and 4,877,747 describe thin-film waveguides which analyze samples when combined with gratings and detectors. For example, U.S. Pat. No. 4,815,843 to Tiefenthaler and Lukosz describes an optical sensor utilizing a diffraction grating applied onto a substrate which transmits coherent light to a sample through a waveguide and to a detector. The waveguide is simply employed to transmit radiation to the detector. The waveguide was also protected with a blocking overcoat so as not to sense the chemical environment directly. Ultra thin coatings on the grating are reacted with antigen-antibody material to modify the refractive index in the grating region. The changed refractive index due to the thin, modified layer above the grating determines the angle of the incoming coherent light beam that is required for entry into the waveguide. This coupling angle determines the concentration of the chemical species through an intermediate refractive index change.

A notable advance in the analytical instrument field was the thin-film spectroscopic sensor found in U.S. Pat. No. 5,082,629 to Burgess and Goldman. This device made use of thin-film waveguide technology for spectroscopic chemical sensing employing broad band, rather than coherent, light sources. The material to be analyzed contacted the waveguide rather than the ultra-thin artificial reaction layer found in the 4,815,843 patent. In the Burgess and Goldman sensor, the grating region is protected to insure that changes in the chemical environment do not affect the angle that incoming radiation is coupled into and out of the waveguide. A pair of diffraction gratings is etched into the top surface of a dielectric substrate. A waveguide is then deposited over the substrate containing the gratings. "White" light is directed at the first grating through the translucent substrate. At a specific angle of incidence, radiation of one wavelength is coupled into the waveguide. Each angle of radiation entering the waveguide is defined by the properties of the grating, waveguide, substrate, and the sample to be analyzed. Thus, a broad range of angles for the incoming radiation is used to insure that a broad range of wavelengths are coupled into the waveguide. Once in the waveguide, the radiation propagates through the same as if it were passing through an optical fiber. Interaction with the sample occurs via a phenomenon known as attenuated total internal reflection (ATR). Although the radiation beam is contained in the thin-film waveguide, a portion of the beam's electric field extends outside the waveguide and into the sample. Each particular sample extracts power from this extended "evanescent" field. After passing through the waveguide, the remaining radiation enters a detector and results in an absorption spectrum of the sample, once a reference signal is obtained. The absorption spectrum then can be related to the concentration of chemical species in the sample. Such propagation of the radiation beam at each wavelength, after interacting with the sample, is coupled through the waveguide and grating at a unique angle. The dispersion of radiation of different wavelengths is compatible with a photodiode array. The differential illumination of particular elements or diodes in the array are easily transferred into a spectrum of the sample, relating absorbance to wavelength.

Although the Burgess and Goldman device, found in U.S. Pat. No. 5,082,629 is a useful device, it suffered from certain disadvantages. For example, the efficiency of the device is limited since the multi-wavelength radiation must first be brought to an entry grating at a variety of angles to insure that different wavelengths are coupled into the waveguide. Unfortunately, only one wavelength of radiation is coupled into the waveguide through the grating at one angle. Other wavelengths directed at the grating at that particular angle are not coupled into the waveguide and are, thus, not used. Such non-accepted wavelengths add to the stray radiation within the device and impair its performance. As an example, assume that the range of angles needed to couple all visible light (red, green, blue, etc.) into the waveguide encompasses 50° and each degree represents one wavelength. Therefore, only 1/50th of the radiation is used at each angle, ie: at each wavelength. Thus, the device can at best be only 2% efficient at each wavelength. Added to this is the fact that the entry and exit gratings possess an efficiency of about 30%. This means that of the 2% starting radiation at each wavelength, only 9% (30% × 30%) at most will reach the exit detector. This reduces the overall efficiency to about 0.2% (9% × 2%). Further reduction in the signal occurs since the inert waveguides composed of materials such as tantalum pentoxide on silica or glass substrates, are typically 50% efficient over a distance of 1 centimeter. Thus the device is realistically only about 0.1% efficient (50% × 0.2%). Waveguides of longer length have greater propogation losses. In the near-infrared region efficiencies of the Burgess and Goldman device range between 0.2 to 0.6%. Consequently, broad band or "white" light sources are not practically utilized with this device.

Edge couplers combined with optical fibers have been proposed. Edge coupling is not efficient. Single-mode optical fibers having small core diameters of 5–7 microns are 20–30 times thicker than the planar waveguides of the type described in the Burgess and Goldman U.S. Pat. No. 5,082,629. Thus, most of the radiation from such couplers will not enter the waveguide, even under the best alignment conditions. Prism couplers must be placed on the waveguide surface and, thus, destroy the ideal planar geometry of the upper surface of the waveguide in contact with the sample being analyzed. In addition, prism couplers do not allow the placement of the radiation source below or to the side of the substrate. Therefore, prism couplers are exposed to potentially chemical environments. Moreover, efficient coupling of light into a waveguide utilizing a prism requires a variable gap between their surface often, dependant upon the size of ambient dust particles. As a result, reproducibility utilizing prism couplers is difficult to achieve. There also exists a problem with selecting index of refractions between the prisms and the waveguide. Many thin-film waveguides have large refractive indices, e.g. greater than 2.0. Only expensive, higher index prisms such as rutile (TiO$_2$) could possibly be used in this scenario.

Tapered waveguides are shown in U.S. Pat. No. 4,711,514. Taper couplers have been described by Tien et al in an article entitled "Radiation Fields of a Tapered Film and a Novel Film-to-Fiber Coupler". The taper described is used as a means to couple monochromatic laser light out of a waveguide into an optical fiber using a fine laser beam. A prism was described as being used to couple radiation into the waveguide. Tien et al also specifically indicated that coupling radiation into a taper is much more difficult and would require further development.

Tamir in Chapter 3 of a work entitled "Integrated Optics" indicated that tapered couplers do not appear to be readily applicable in the "leaky-wave theory" that proved to be so useful in dealing prism and grating couplers. The reason given was that the incident surface wave was converted very rapidly to outgoing radiation because the surface-wave mode reaches cut-off conditions in the taper. It was believed that energy was scattered over a wide spectrum of radiation modes, so that a "leaky-wave" cannot be established. Tamir also stated that using a tapered coupler as an input coupler possesses a very small efficiency and is difficult to align and match the form of the incident beam. Tamir also states that due to these disadvantages, "little theoretical efforts have been spent on investigating tapered couplers"

A waveguide-type of spectrometer using broad-band radiation as a source in analyzing chemical samples efficiently would be a great advance in the instrumentation field.

SUMMARY OF THE INVENTION

In accordance with the present invention a novel, efficient, and useful broad band waveguide spectrometer is herein described.

The spectrometer of the present invention analyzes a sample of material by utilizing a source of electromagnetic radiation and a detector. The spectrometer includes a waveguide which possesses an entry and exit for the electromagnetic radiation emanating from the source. The source may be "white light" coherent light, and the like In certain cases, the light may be ultraviolet light or near-infrared light. A waveguide may be formed by depositing a thin film of high refractive index material over a substrate material having a lower refractive index. For example, the waveguide material may be composed of tantalum pentoxide (Ta$_2$O$_5$), while the substrate may be formed of fused silica (SiO$_2$). The waveguide would possess a surface, preferably opposite the interface between the waveguide and the substrate, which would support a sample of material to be analyzed. Such analysis is known as attenuated total internal reflection (ATR). That is to say, radiation which passes through the thin-film waveguide interacts with the sample supported by the surface of the waveguide. It is believed that a portion of the electric field of the electromagnetic radiation passing through the waveguide extends into the sample which absorbs a portion of the same at a particular wavelength. Thus, less power is available for the electromagnetic beam which passes through the waveguide exit of the same.

Capturing means is included for directing electromagnetic radiation passing from the exit of the waveguide to the detector. Such capturing means may take the form of a grating formed at the interface between the waveguide and the substrate or on top of the waveguide. Capturing means may also take the form of an edge, a prism, or a taper coupler. Moreover, the electromagnetic radiation exiting the waveguide would be sent to a detector such as a photodiode array detector which is capable of detecting radiation from the waveguide in which the wavelengths are dispersed. In addition, diverging electromagnetic radiation exiting the waveguide may be condensed unto the detector using optical means.

Coupling into the waveguide is achieved by a taper portion of the entrance of the waveguide i.e. a taper coupler. A taper coupler may have a shallow slope greater than 2,000:1. In addition, the taper coupler width may be in excess 3 mm to enhance the possibility that more incident light will be coupled into the waveguide. It has been found that measurements of entering and exiting light from the waveguide, via the taper coupler, result in overall efficiencies which are tenfold greater than efficiencies achieved using gratings to couple light into the waveguide.

The taper region may also possess a coating which is thicker than the evanescent penetration distance into the sample at the surface of the waveguide. This minimizes effects due to changing sample properties such as refractive index, and defines the edges of the sample relative to the beam through the waveguide. Preferably, the coating may be eliminated by the confining of the sample to the surface which lies between the taper and the exit or grating, e.g.: wicking the sample under a microscope cover slip. Where the waveguide is to be employed with highly absorbing chemical species, as well as weakly absorbing chemical species, a thick, non-reacting, partially blocking coating may be placed over the waveguide between the entrance taper and the exit grating over the portion of the surface interacting with the electromagnetic radiation in the waveguide. In addition, a thinner coating may cover the surface of the waveguide at the interface with the sample being analyzed, but would be of a lesser thickness to allow interaction dependent on the type of electromagnetic radiation passing through the waveguide. For example, infrared light requires a thicker coating than ultraviolet light.

The waveguide portion of the present invention may also be formed in the shape of a prism and possess an exit taper coupler for dispersing radiation laterally from the waveguide in its plane, and exiting toward the detector. In this regard, the entry taper coupler may be convex and act to focus several parallel beams of radiation, similar to using a standard plano-convex lens with a collimated beam of radiation. It is also important to separate the waveguide beam from the incoupling beam reflected into the substrate. Where a significant portion of the radiation incident upon the taper coupler is at very shallow angles below the surface of the substrate, some radiation is reflected back into the substrate. Unfortunately a portion of this substrate radiation may reach the detector near the waveguide beam and cause interference. Thus, a prism-shaped waveguide disperses radiation so as not to cause this interference at the detector.

Another embodiment producing this dual path arrangement, requires that an overcoat be deposited on the waveguide at the portion of the surface where interaction occurs between the sample and the waveguide. Thus, one beam would interact with the sample while another would pass through the waveguide without interaction or with reduced interaction. Also, two coatings may be placed over the surface permitting interaction with the sample, one of a thickness preventing sample interaction and the other allowing limited interaction with the sample. In any case, a dual beam operation is produced for spectroscopic referencing.

It may be apparent that a novel and useful spectrometer for analyzing samples of material has been described.

It is therefore an object of the present invention to provide a high efficiency spectrometer for analyzing a sample utilizing a thin-film waveguide which permits the use of "white" light.

It is another object of the present invention to provide a spectrometer for analyzing a sample of material which utilizes a novel taper coupler, and, thus, eliminates the inefficient input grating coupler of the prior art.

Another object of the present invention is to provide a spectrometer for analyzing a sample of material which solves the problem of interference between radiation that is not coupled into the waveguide with radiation that passes through the waveguide for interaction with a sample of material.

Yet another object of the present invention is to provide a spectrometer for analyzing a sample of material which is capable of producing a dual beam of light within a thin-film waveguide, one for analyzing the sample and one for serving as a reference beam.

A further object of the present invention is to provide a spectrometer analyzing a sample of material which is capable of operating efficiently in the near-infrared visible, and ultraviolet regions and is further capable of adjusting to different radiation absorbing characteristics of the sample being analyzed.

Yet another object of the present invention is to provide a spectrometer which eliminates problems associated with sample contamination, changes in the spectroscopic window, and instrument problems due to temperature changes on internal optics, by measurement with two different path lengths simultaneously.

The invention possesses other objects and advantages especially as concerns particular characteristics and features thereof which will become apparent as the specification continues.

For a better understanding of the invention reference is made to the following detailed description of the preferred embodiments thereof which will be referenced to the prior described drawings.

DESCRIPTION OF THE PREFERRED EMBODIMENTS

Various aspects of the present invention will evolve from the following detailed description of the preferred embodiments which should be taken in conjunction with the prior described drawings.

Figure 1:
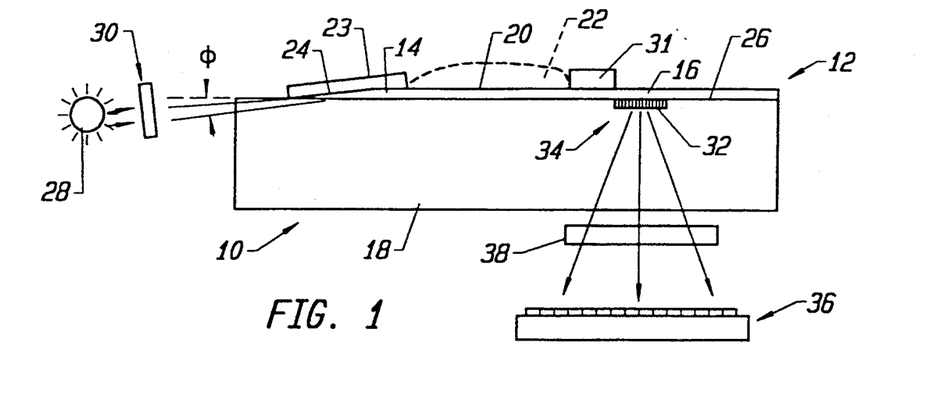
FIG. 1 is a schematic side elevational view of the spectrometer of the present invention.
Figure 2:
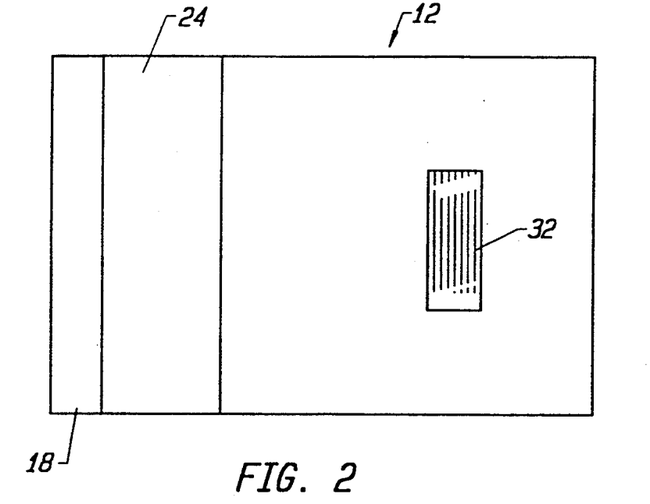
FIG. 2 is a schematic top plan view of the spectrometer of FIG. 1.

The invention as a whole is depicted in FIG. 1 and indicated by reference character 10. The spectrometer 10 includes as one of its elements a thin-film, single mode, waveguide 12 which includes an entry region 14 and an exit region 16. Waveguide 12 is composed of a high refractive index material such as tantalum pentoxide ($Ta_2O_5$). The thickness of waveguide 12 is exaggerated in FIG. 1, but is generally less than 0.35 microns designed to maintain single mode propagation. Waveguide 12 is placed atop a substrate 18 of transparent material having a refractive index somewhat less than waveguide 12. For example, substrate 18 is composed of silicate ($SiO_2$) having a refractive index of 1.444 using near infrared light. Spectrometer 10 includes an upper surface 20 which may be capable of interacting with a sample to be analyzed 22, depicted in phantom in FIG. 1.

Waveguide 12 includes a tapered portion 24 i.e. a taper coupler for entry 14. Entry taper 24 may be fabricated by sputtering, plasma, vapor depositing the appropriate taper with the waveguide. Other known methods may be used for this purpose. A portion of the substrate is protected by a mask during this process. Taper couplers such as entry taper 24 can also be constructed by diffusing the waveguide 12 into substrate 18 at interface 26, leaving a tapered edge to the waveguide 12. A taper coupler retains the planar geometry of interface 26. Also, taper coupler such as tapered portion 24 may be employed to couple light into waveguide 12 from the side of substrate 18 to protect the light source 28 from the chemical environment of sample 22. It has been found that taper portion 24 significantly increases the efficiency of spectrometer 10 over the prior art, and is especially useful when using a broad-band light source 28. It is anticipated that taper portion 24 may possess a slope of at least 2,000:1, although steeper slopes may be used. With further reference to FIG. 1, it may be observed that light emanating from source 28 will strike substrate 18 and waveguide 12 at an angle "phi". In general, taper coupler 24 permits all permissible wavelengths of light to be coupled into waveguide 12 from the side of substrate 18 at a very narrow range of angles. Relatively thick overcoat regions 29 and 31 may be formed on waveguide 12 to confine the sample 22 between entry 14 and exit 16. Also overcoat regions 29 and 31 protect entry 14 and exit 16 from contact which affects the output signal through grating 32.

Optical means 30 may take the form of a fiber optic element, a prism, a filter, a slit, a lens, a polarizer, or any combination of these.

Grating 32 causes electromagnetic radiation to the exit region 16 of thin film waveguide 12 and serves as capturing means 34 for directing electromagnetic radiation passing from exit region 16 to detector 36. Detector 36 may be a single Indium Gallium Arsenide (InGaAs) photodiode array or several individual detectors. Optics 38 also serve as part of capturing means 34 and may take the form of a lens, slit, prism, and the like.

Figure 9:
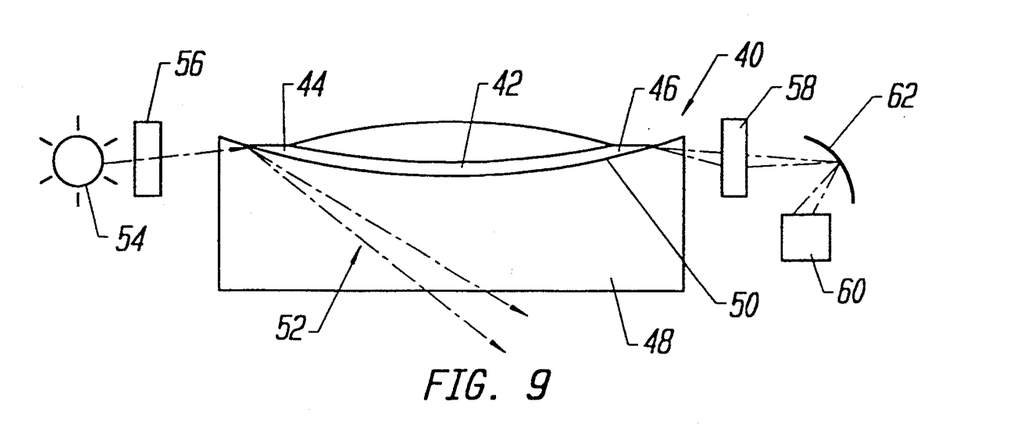
FIG. 9 is a schematic view, depicting a further embodiment of the spectrometer of the present invention utilizing tapered portions at the exit and entrance to the waveguide.

With reference to FIG. 9, spectrometer 40 is shown utilizing a waveguide 42 of similar material to waveguide 12 of FIG. 1. However, waveguide 42 includes an entrance taper coupler 44 and an exit taper coupler 46 on a substrate 48 within nonplanar interface 50, to separate radiation exiting taper 46 from substrate electromagnetic radiation (represented by rays 52), that did not couple into waveguide 42 from electromagnetic radiation source 54. It should be noted that when optical portions 56 and/or 58 are employed, such optical portions may include fiber optic devices known in the art. In this way spectrometer 40 may be used as a probe since it is separated from source 54 and detector 60 by such fiber optics. Optical dispersing grating element 62 is also shown in FIG. 9.

Figure 3:
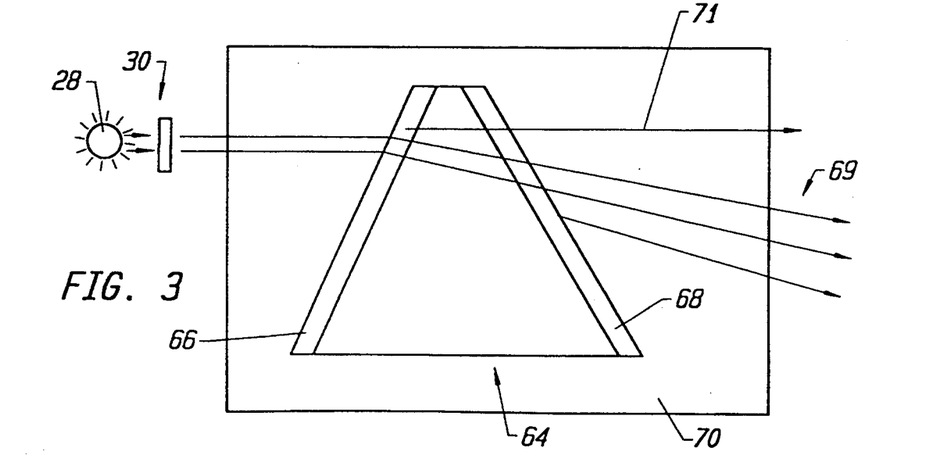
FIG. 3 is a schematic top plan view of another embodiment of the spectrometer of the present invention.

FIG. 3 depicts a waveguide 64 utilizing entrance and exit taper 66 and 68 with substrate 70. Waveguide 64 illustrates that entry and exit tapers 66 and 68 may be employed in nonparallel alignment to disperse waveguide radiation beams 69 exiting from waveguide 64, in the plane of waveguide 64. This provides separation of beams 69 from the primary substrate beam 71 which never leaves substrate 70.

Figure 4:
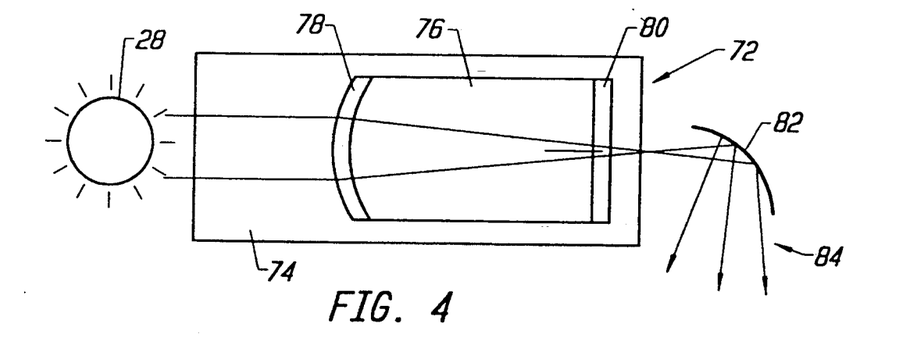
FIG. 4 is a schematic top plan view of yet another embodiment of the spectrometer of the present invention.

FIG. 4 also illustrates a spectrometer 72 of the present invention possessing a substrate 74 and a waveguide 76. Waveguide 76 is of the thin-film type such as waveguide 12. However, waveguide 76 includes a curved tapered entry portion 78 combined with a straight tapered exit coupler 80. Again, external grating 82 creates dispersed waves 84 to achieve the same end as the embodiment depicted in FIG. 3.

Figure 5:
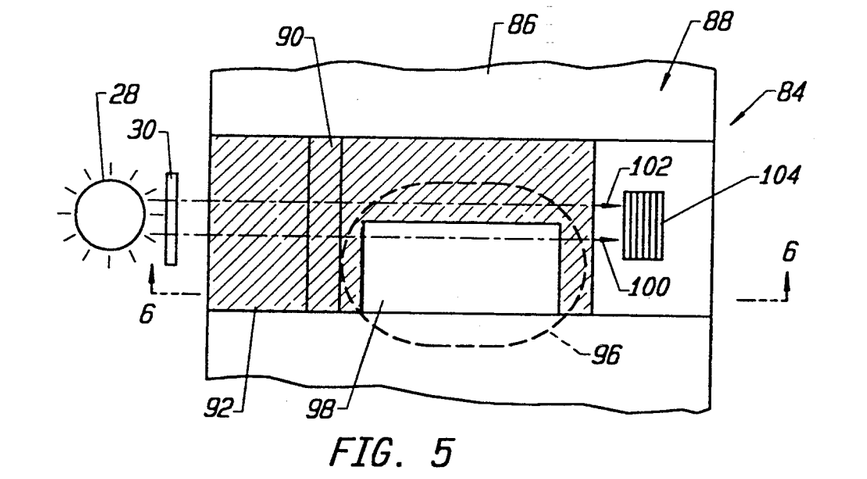
FIG. 5 is a schematic top plan view of the dual beam producing version of the spectrometer of the present invention.
Figures 6, 6A:
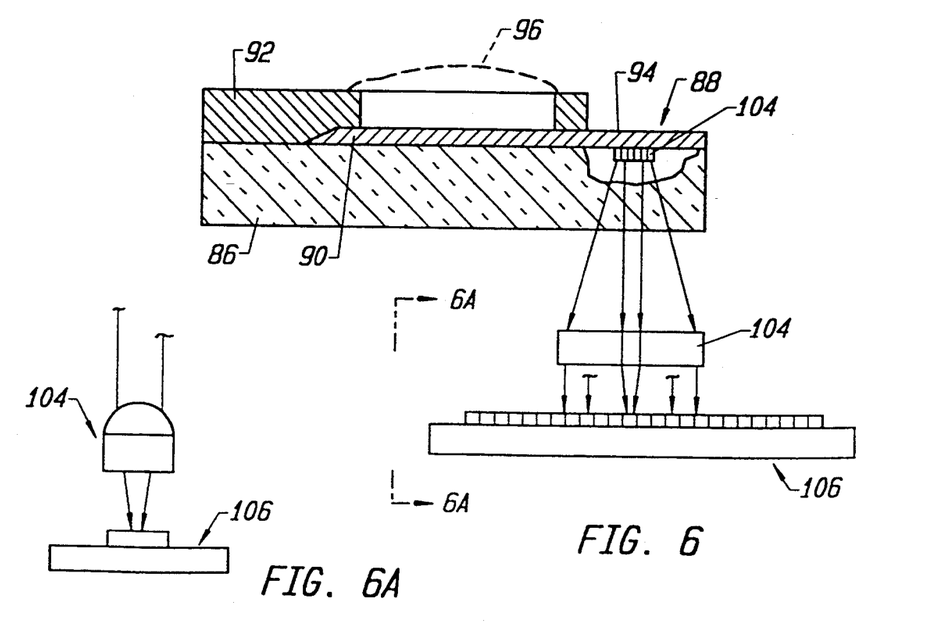
FIG. 6 is a sectional view taken along line 6—6 of FIG. 5.
FIG. 6A is a end elevational view taken along line 6A—6A of FIG. 6.

Turning to FIGS. 5 and 6, a self referencing spectrometer 84 is depicted. Spectrometer 84 includes a substrate 86 and a thin-film waveguide 88, similar to waveguide 12. Waveguide 88 includes an entrance taper portion 90. It is believed that by making measurements with two different beams through a spectrometer, many spectroscopic measurement problems are eliminated or minimized.

The addition, the embodiment shown in FIGS. 5 and 6 employs a coating 92, exaggerated in size in FIGS. 5 and 6 for emphasis. Coating 92 lies over waveguide 88 leaving a area 98 of surface 94, thereof without a coating. Thus, a sample 96 may be placed over uncoated area 98 as well as coated surface 92 of surface 94. Light ray 100 emanating from source 28 may be used to pass through waveguide 88 and uncoated portion 98 to analyze sample 96. Other light ray 102 may pass through waveguide 88 without interacting with sample 96 since coating 92 prevents such interaction. Condensing lens 104 again aids to capture the electromagnetic radiation exiting spectrometer 84 and pass the same to array detector 106, FIG. 6A.

Figure 7:
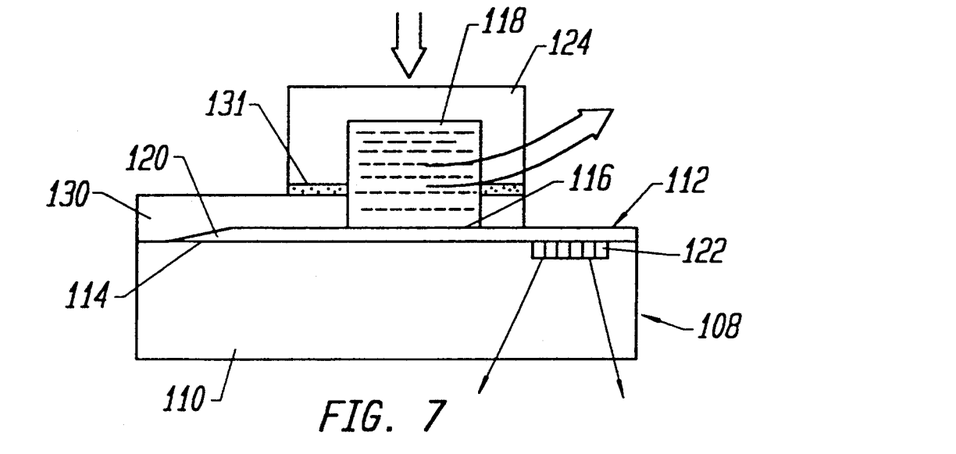
FIG. 7 is a schematic end view of a continuous flow version of the spectrometer of the present invention.
Figure 8:
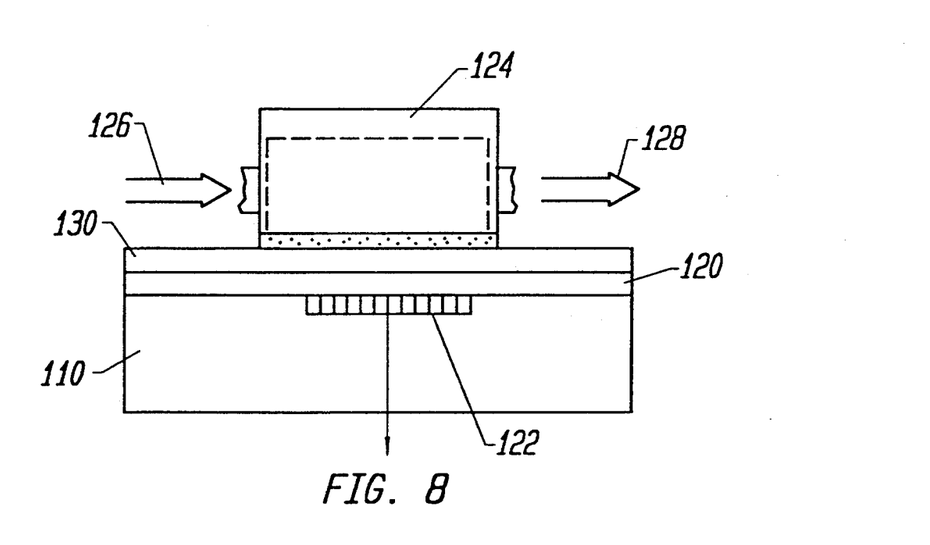
FIG. 8 is a schematic end elevational view of the continuous flow version of the spectrometer of the present invention depicted in FIG. 7.

The present invention also encompasses spectrometer 108 depicted in FIGS. 7 and 8. Spectrometer 108 employs a substrate 110 having a thin-film waveguide 112 on interface 114. Waveguide surface 116 permits interaction between sample 118 and the electromagnetic radiation passing through waveguide 112. Also, waveguide 112 includes an entrance taper portion 120 such as the one depicted in FIG. 1. Grating 122 again serves to capture electromagnetic radiation exiting waveguide 112 and directing the same to a detector (not shown). Sample 118 is found in a flow cell 124 which permits the continuous flow of sample therethrough, (or static containment thereof) directional arrows 126 and 128. Overcoat 130 on substrate 110 again permits the use of spectrometer in this continuous manner by permitting flow cell 124 to bond to the same. Bonding to overcoat 130 eliminates unwanted spectral signals and chemical interaction problems caused by the bonding material or physical seals 131, FIG. 7.

The following examples are included for the purposes of illustration but are not intended to limit the scope of the invention unless otherwise indicated.

EXAMPLE I

Figure 10:
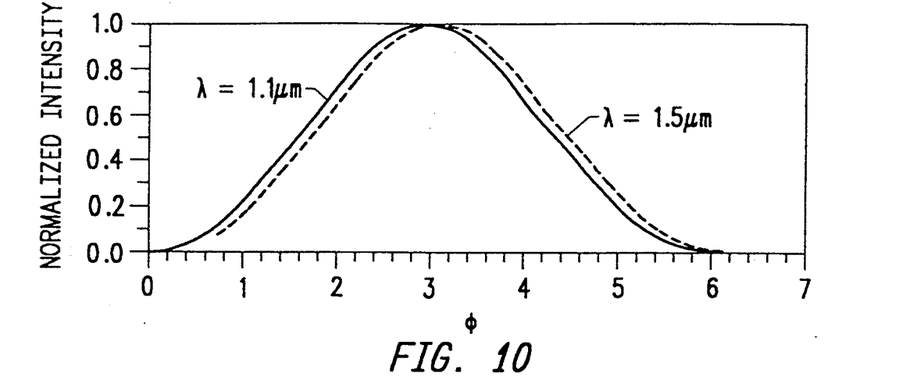
FIG. 10 is a graphical representation of calculated intensity at angle "phi" for separate wavelengths of electromagnetic radiation.

A spectrometer was constructed applying a tapered coupler of the type depicted in FIG. 1. A silica ($SiO_2$) substrate was employed having a refractive index of 1.444 in the near infrared. Atop the substrate, a thin-film waveguide was formed having a thickness of 0.35 microns. The waveguide was formed of tantalum oxide ($Ta_2O_5$) possessing a refractive index of 2.02. The taper portion of the entrance to the waveguide possessed a slope of 10,000:1. Calculations were made for two different wavelengths of electromagnetic radiation in the near-infrared region e.g. 1.1 and 1.5 microns. FIG. 10 represents a calculation of the energy distribution as a function of the angle below the upper surface of the substrate. The results show that the peak of the energy distribution remains near 3° below the surface of the substrate in this wavelength range. The overall energy distribution is also similar at both wavelengths. An inference may be drawn that energy distribution is similar at all intermediate wavelengths. Consequently, the taper coupler portion allowed all wavelengths to be coupled into the waveguide from the side of the substrate at a very narrow range of angles. Thus, the taper coupler makes an excellent broad band coupler for thin-film waveguides.

EXAMPLE II

Employing a fused silica substrate, two grating couplers separated by one centimeter were etched into the same. With reference to FIG. 1, the second grating would appear to the right of the grating shown therein. Each grating possessed 909 grooves/millimeter and were etched 0.1–0.15 microns into the substrate. A tantalum pentoxide ($Ta_2O_5$) waveguide was deposited on the substrate and over the gratings. The waveguide was terminated with a tapered portion, as shown in FIG. 1 about 10 mm from the left edge of the substrate. The thickness of the waveguide was 0.25 microns to ensure single-mode propagation in the near-infrared. The slope of the taper was approximately 12,000:1, producing a taper width of about 3 mm. This apparatus thus, may compare coupling radiation efficiencies using either a taper or a grating as the entrance to the waveguide. In both cases, a grating was used to couple light exiting the waveguide for detection. A large area, single element InGaAs detector was employed. The detector was responsive to radiation in the 1.1 to 1.7 micron wavelength region i.e. the near-infrared. The detector was connected to a power meter and used to measure the power of the laser beam illuminating the incoupling grating, and the power of the resulting beam coupled out of the outcoupling grating. In this regard, a 2 milliwatt Helium-Neon (HeNe) laser operating at a wavelength of 1.523 microns was used as a radiation source. The light from the laser was polarized by a polarizer for coupling into the TM(0) mode (polarization normal to the grooves in the grating). A condensing lens was employed to produce a beam spot diameter at the incoupling grating of about 0.25 mm. The waveguide was rotated relative to the incoupling laser beam to achieve maximum coupling into the TM(0) mode. This occurred at about 5 degrees from vertical (normal) to the substrate surface. The overall efficiency of the device using the two grating (a prior art device) as the entrance and exit couplers was measured to be 0.3%.

EXAMPLE III

The apparatus described in Example II was then modified to couple radiation into its waveguide through the taper described. Using the taper as an entrance coupler, a 256 element InGaAs detector array was used. The output of the 1.523 Helium-Neon laser was formed into the image of a narrow rectangular metal slit and focusing optic. The image from the optic was focused onto the side of the substrate, as shown in FIG. 1, until maximum coupling was achieved into the waveguide through the entrance. The maximum intensity was found at an angle "phi" of about 3° (below the substrate). After measuring the power of the laser beam coupled out of the waveguide by the grating, the waveguide was removed from the substrate and the power of the laser beam was measured with the array detector in place. The resulting overall efficiency was determined to be 5.3%. Thus, a greater than ten fold improvement in efficiency was obtained over the system using a prior art grating to couple light into the waveguide, described in Example II and U.S. Pat. No. 5,082,629.

EXAMPLE IV

Figure 11:
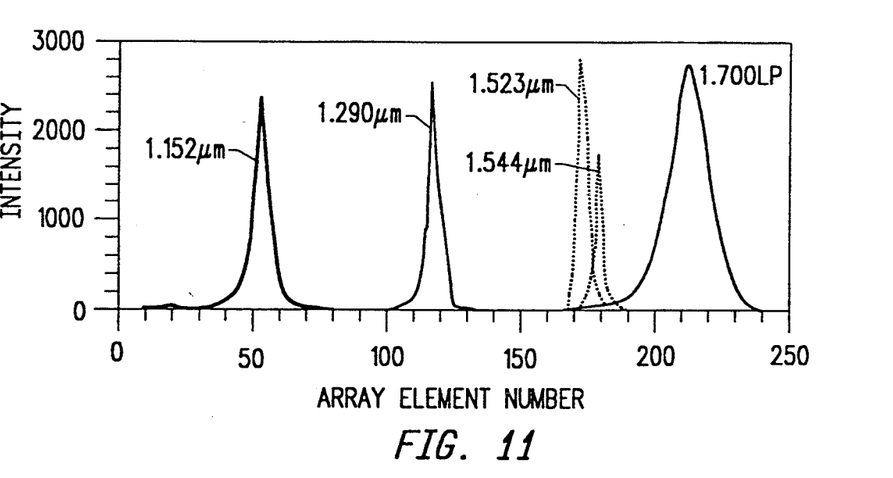
FIG. 11 is a graphical representation of the measured intensity exiting the spectrometer of FIG. 1 plotted against array element numbers of the detector.

Employing the tapered coupler to the entrance of the waveguide described in Example III, a twenty Watt Tungsten white light source was employed. Again, the InGaAs detector array was used to receive light exiting through the grating waveguide. A metal slit was also employed. the focusing optics included a 500 micron diameter, 0.22 numerical aperture optical fiber. FIG. 11 shows the detection of a variety of known wavelength sources using this apparatus. The peaks in FIG. 11 represent TM polarization. It may be obvious that the signal intensity is plotted against the photodiode element number of the detector array. A calibration can be established from this information to mathematically convert element number into wavelength. The peak labeled 1.544 micron originated from the Tungsten white light source and a 1.544 micron narrow-band interference filter. A Helium-Neon laser was then substituted for the Tungsten white light source. The peaks labeled 1.152 microns and 1.523 microns in FIG. 11 represent the Helium-Neon laser light passed into the waveguide at wavelengths 1.152 and 1.523 microns. Subsequently, a diode laser was substituted for the Helium-Neon laser. The peak labeled 1.290 microns represents the wavelength of light from the diode laser. The peak labeled 1.700LP represent light originating from the white light source which was passed through a 1.700 micron long-pass filter. It was found that the InGaAs detector array decreased in sensitivity at wavelengths longer than 1.7 microns giving rise to the appearance of a peak.

EXAMPLE V

Figure 12:
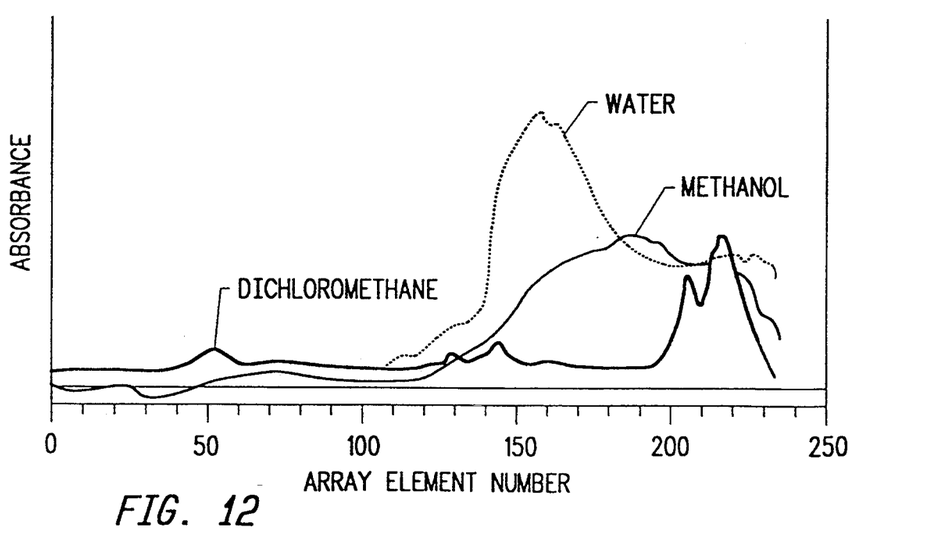
FIG. 12 is a graphical representation of absorbance for different chemical species with respect to certain element array numbers of the detector using the spectrometer of FIG. 1.
Figure 13:
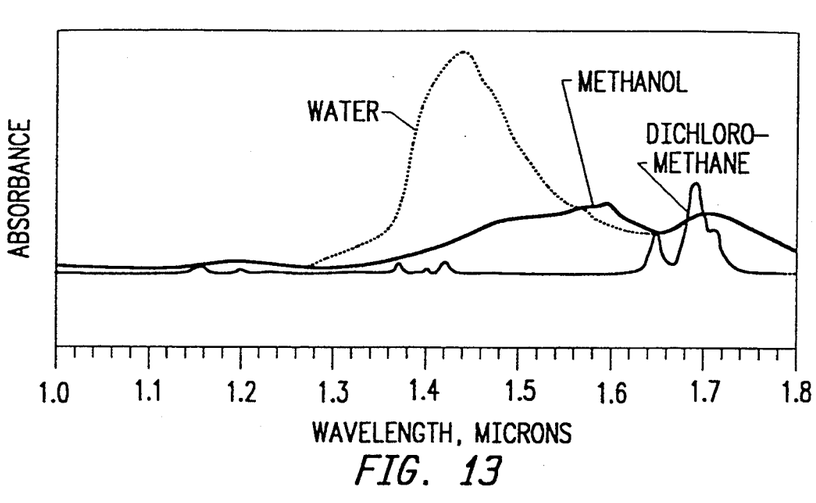
FIG. 13 is the absorbance measured against the wavelength by prior art transmission methods using a one millimeter wide cuvette filled with liquids and a prior art commercially available spectrometer.

Utilizing the taper entry and grating exit described in FIG. 1, examples of water, methanol, and dichloromethane were employed as samples utilizing a Tungsten white light source and a TM polarization. FIG. 12 represents a plot of the absorbance verses the array element number. Such channel or array element numbers can be related to the wavelengths. This relationship is illustrated in FIG. 11. Spectra appearing in FIG. 13 is measured by conventional transmission in 1 mm wide cuvettes and are very similar to the results shown in FIG. 12.

EXAMPLE VI

Figure 14:
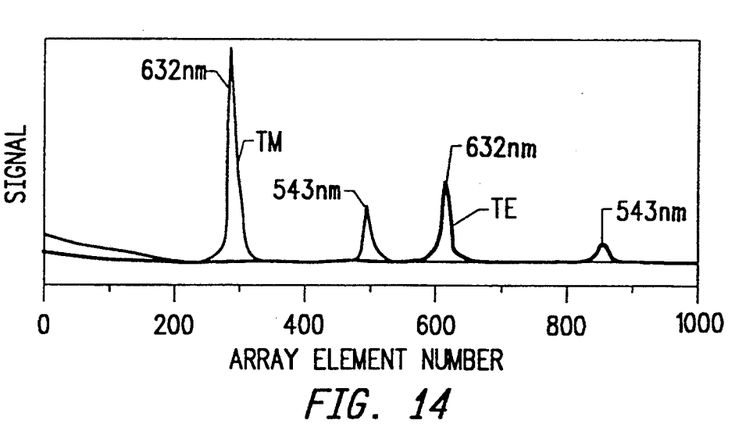
FIG. 14 is a graphical representation of the polarized signals using two lasers employing the embodiment of the invention in FIG. 1.

A prism-shaped waveguide was fabricated similar to the one depicted in FIG. 3. Two Helium-Neon laser beams having wavelengths of 0.543 and 0.632 microns were combined and directed toward the leading taper coupler at the entrance of the waveguide. The resulting refraction separated these wavelengths, as did their respective polarizations. A 1024 element silicon photodiode array was used to detect these radiations dispersed from the prism-shaped waveguide. The results are presented in FIG. 14. It was concluded that the primary (non-coupled) reflected beam in the substrate did not impinge upon the detector, thereby demonstrating that entry and exit tapers, not normal to the direction of the beam have successfully separated this radiation from the waveguide radiation.

EXAMPLE VII

Figure 15:
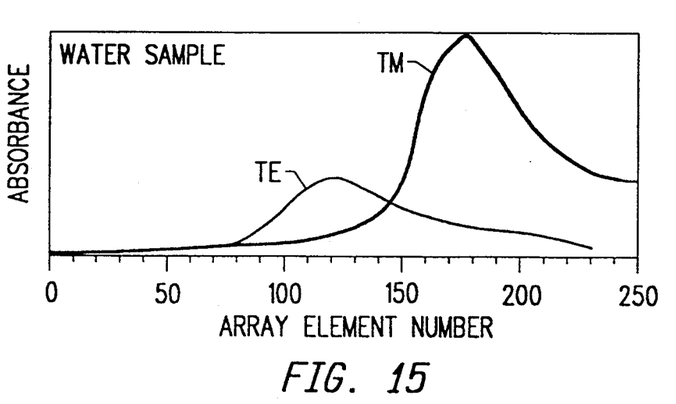
FIG. 15 is a graphical representation of the absorbance of a water sample using TE and TM samples plotted against array element numbers using the embodiment of the invention in FIG. 1.

The waveguide having the taper coupler illustrated in FIG. 1 was employed to analyze water. The optical means illustrated in FIG. 1 included a polarizer which was rotated 90° to change from TE to TM polarization. The water was analyzed using both polarizations. The spectrum of water was less intense by a factor of about 2.5 in the TE polarization. The maximum absorbance in both spectrum represent a wavelength of about 1.450 millimicrons. They were shifted because same wavelength of each polarization is coupled out of a high index waveguide at a different angle by the exit diffraction grating. Wavelength calibration procedures, such as that illustrated in FIG. 11, can be used to convert each spectrum into absorbance verses wavelength. The data shown in FIG. 15 indicates that TE and TM are sufficiently displaced from each other. Also, this means that TE polarization extends to longer wavelengths in FIG. 15 than TM polarization. Likewise, TM polarizations extend to shorter wavelengths than TE. This extends the useable wavelength range of the device than would otherwise be achieved with just one polarization.

While in foregoing, embodiments of the present invention have been set forth in considerable detail for the purposes of making a complete disclosure of the invention, it may be apparent to those of skill in the art that numerous changes may be made in such details without departing from the spirit and principles of the invention.

What is claimed is:

1. A spectrometer for analyzing a sample of material by utilization of an electromagnetic radiation source and a detector comprising:
   a. a waveguide possessing an entry for admission of electromagnetic radiation from the source and an exit for the electromagnetic radiation emanating from the source, said waveguide further including a surface between said entry and exit portions, permitting interaction between electromagnetic radiation passing through said waveguide and a sample of material, said waveguide exit permitting electromagnetic radiation from the waveguide to pass from said waveguide;
   b. a tapered portion forming a part of said entry of said waveguide, said tapered portion coupling electromagnetic radiation emanating from the source to said waveguide;
   c. a substrate adjacent said waveguide, said substrate being capable of passing electromagnetic radiation from the source to said tapered portion forming part of said waveguide entry; and
   d. capturing means for directing electromagnetic radiation passing from said exit of said waveguide to a detector.

2. The spectrometer of claim 1 in which said capturing means comprises a grating formed at said exit of said waveguide.

3. The spectrometer of claim 1 in which said capturing means comprises an edge formed at said exit of said waveguide.

4. The spectrometer of claim 1 in which said capturing means comprises a prism placed at said exit of said waveguide.

5. The spectrometer of claim 1 in which said capturing means comprises a tapered coupler formed at said exit of said waveguide.

6. The spectrometer of claim 1 which additionally comprises optical means for altering the electromagnetic radiation traveling between the source and the tapered portion of said entry.

7. The spectrometer of claim 6 in which said optical means comprises a fiber optic element.

8. The spectrometer of claim 6 in which said optical means comprises a lens.

9. The spectrometer of claim 6 in which said optical means comprises a filter.

10. The spectrometer of claim 9 in which said filter comprises polarizing filter.

11. The spectrometer of claim 1 in which said tapered portion increases uniformly in thickness from an edge to the thickness of the coupled waveguide.

12. The spectrometer of claim 1 in which said substrate includes a material possessing lower refractive index than said waveguide.

13. The spectrometer of claim 1 which additionally comprises channel means for permitting continuous flow of the sample across said surface of said waveguide.

14. The spectrometer of claim 1 in which said substrate includes a non planar surface, and said waveguide being formed on said non planar substrate surface.

15. The spectrometer of claim 14 in which additionally includes a fiber optic element conducting electromagnetic radiation from the source to said waveguide entry, and a fiber optic element exiting said waveguide to said capturing means.

16. A spectrometer for analyzing a sample of material by utilization of an electromagnetic radiation source and a detector comprising:
   a. a waveguide possessing an entry for admission of electromagnetic radiation from the source and an exit for the electromagnetic radiation emanating from the source, said waveguide further including a surface between said entry and exit portions, permitting interaction between electromagnetic radiation passing through said waveguide and a sample of material, said waveguide exit permitting electromagnetic radiation from the waveguide to pass from said waveguide;
   b. a tapered portion comprising a curved body, said tapered portion forming a part of said entry of said waveguide, said tapered portion coupling electromagnetic radiation emanating from the source to said waveguide; and
   c. capturing means for directing electromagnetic radiation passing from said exit of said waveguide to a detector.

17. A spectrometer for analyzing a sample of material utilizing an electromagnetic radiation source and a detector, comprising:
   a. a waveguide possessing an entry and an exit for the electromagnetic radiation emanating from the source, said waveguide further including a material of a certain refractive index having a surface, between said entry and exit portions, permitting interaction between electromagnetic radiation passing through said waveguide and a sample of material, said waveguide exit permitting electromagnetic radiation in the waveguide to pass from said waveguide;
   b. a tapered portion forming at least a part of said entry of said waveguide, said tapered portion coupling electromagnetic radiation emanating from the source to said waveguide;
   c. a coating on a portion of said waveguide surface of said waveguide of sufficient thickness to measurably reduce interaction of the electromagnetic radiation with the sample, said coating including a material possessing a lower refractive index than the material included in said waveguide; and
   d. capturing means for directing electromagnetic radiation that has interacted with the sample, passing from said exit of said waveguide to a detector.

18. The spectrometer of claim 17 in which said coating on said waveguide surface possesses a thickness of at least 0.2 microns.

19. The spectrometer of claim 17 which further comprises recondensing means for steering electromagnetic radiation exiting said waveguide to the detector.

20. The spectrometer of claim 17 which additionally comprises optical means for altering the electromagnetic radiation traveling between the source and the tapered portion of said entry.

21. A spectrometer for analyzing a sample of material utilizing an electromagnetic radiation source and a detector, comprising:

a. a waveguide possessing an entry and an exit for the electromagnetic radiation emanating from the source, said waveguide further including a surface between said entry and exit portions, permitting interaction between electromagnetic radiation passing through said waveguide and a sample of material, said waveguide exit permitting electromagnetic radiation in the waveguide to pass from said waveguide;

b. a tapered portion forming at least a part of said entry of said waveguide, said tapered portion coupling electromagnetic radiation emanating from the source to said waveguide;

c. a coating on a portion of said waveguide surface of said waveguide of sufficient thickness to measurably reduce interaction of the electromagnetic radiation with the sample, said coating including at least a first portion and a second portion, said first portion of said coating possessing a thickness less than said second portion of said coating; and d. capturing means for directing electromagnetic radiation that has interacted with the sample, passing from said exit of said waveguide to a detector.

22. The spectrometer of claim 21 in which said first and second portions of said coating thicknesses are less than the evanescent penetration depth of the electromagnetic radiation passing through said waveguide.

* * * * *